(12) United States Patent
Gigi et al.

(10) Patent No.: US 11,730,585 B2
(45) Date of Patent: Aug. 22, 2023

(54) TISSUE REPAIR DEVICE AND METHOD

(71) Applicants: The Medical Research, Infrastructure, and Health Services Fund of the Tel-Aviv Medical Center, Tel-Aviv (IL); Ramot at Tel-Aviv University Ltd., Tel Aviv (IL)

(72) Inventors: Roy Gigi, Tel-Aviv (IL); Mickey Scheinowitz, Kfar Saba (IL); Noaa Reisman, Tel-Aviv (IL); Itzhak Mallayev, Tel-Aviv (IL); Roman Ziv, Tel-Aviv (IL); Sivan Goldin, Tel-Aviv (IL)

(73) Assignees: Ramot at Tel-Aviv University Ltd., Tel-Aviv (IL); The Medical Research, Infrastructure, and Health Services Fund of the Tel-Aviv Medical Center, Tel-Aviv (IL)

( * ) Notice: Subject to any disclaimer, the term of this patent is extended or adjusted under 35 U.S.C. 154(b) by 273 days.

(21) Appl. No.: 16/325,707

(22) PCT Filed: Nov. 15, 2017

(86) PCT No.: PCT/IL2017/051241
§ 371 (c)(1),
(2) Date: Feb. 14, 2019

(87) PCT Pub. No.: WO2018/092129
PCT Pub. Date: May 24, 2018

(65) Prior Publication Data
US 2020/0121315 A1 Apr. 23, 2020

Related U.S. Application Data

(60) Provisional application No. 62/422,172, filed on Nov. 15, 2016.

(51) Int. Cl.
*A61B 17/11* (2006.01)
*A61F 2/08* (2006.01)
*A61B 17/04* (2006.01)

(52) U.S. Cl.
CPC ........ *A61F 2/0811* (2013.01); *A61B 17/0401* (2013.01); *A61B 17/0487* (2013.01);
(Continued)

(58) Field of Classification Search
CPC ... A61B 17/1146; A61B 17/083; A61B 17/08; A61B 17/10; A61B 17/105;
(Continued)

(56) References Cited

U.S. PATENT DOCUMENTS 3,378,010 A    4/1968  Coding et al.
5,649,937 A *  7/1997  Bito ................... A61B 17/1285
                                                        606/151

(Continued)

FOREIGN PATENT DOCUMENTS

CN      205041494 U    2/2016
WO   WO 1999/062407 A1  12/1999

OTHER PUBLICATIONS

International Preliminary Report on Patentability received in PCT Application No. PCT/IL2017/051241, dated May 21, 2019.
(Continued)

*Primary Examiner* — Wade Miles
(74) *Attorney, Agent, or Firm* — Knobbe, Martens, Olson & Bear, LLP (57) ABSTRACT

Repair devices and methods allow better contact between two tissues, such as tendon and bone for better healing process. The repair device is used for re-attaching and securing a torn tissue in place or realigning torn edges back together, or connecting any two tissues. The device includes a tissue attachment, a clamp and a binder and/or an anchor.

29 Claims, 8 Drawing Sheets

(52) U.S. Cl.
CPC ....... *A61B 17/1146* (2013.01); *A61B 17/0469* (2013.01); *A61B 2017/0409* (2013.01); *A61B 2017/0488* (2013.01)

(58) Field of Classification Search
CPC .............. A61B 17/128; A61B 17/1285; A61B 2017/1132; A61F 2/0811
See application file for complete search history.

(56) References Cited

U.S. PATENT DOCUMENTS

| | | | |
|---|---|---|---|
| 5,800,544 | A | 9/1998 | Demopulos et al. |
| 2012/0015029 | A1 | 6/2012 | Miller |
| 2013/0066341 | A1* | 3/2013 | Ketai ................... A61F 2/2466 606/151 |
| 2013/0153628 | A1 | 6/2013 | Euteneuer |
| 2015/0024581 | A1 | 9/2015 | Linder et al. |
| 2016/0000445 | A1* | 1/2016 | Raybin ............ A61B 17/00234 606/157 |

OTHER PUBLICATIONS

International Search Report and Written Opinion received in PCT Application No. PCT/IL2017/051241, dated Mar. 12, 2018.

* cited by examiner

Fig. 6 tendon

TISSUE REPAIR DEVICE AND METHOD

This application is the U.S. National Phase under 35 U.S.C. § 371 of International Application No. PCT/IL2017/051241, filed Nov. 15, 2017, designating the U.S., and published in Spanish as WO 2018/092129 A1 on May 24, 2018, which claims priority to U.S. Provisional Application No. 62/422,172, filed Nov. 15, 2016, the entire contents of which are incorporated herein by reference.

FIELD OF THE INVENTION

The present invention relates in general to the field of tissue repair. Specifically, the invention provides devices and methods for allowing better contact between two tissues, such as tendon and bone for better healing process.

BACKGROUND OF THE INVENTION

Known surgical methods of rotator cuff repair (open, mini-open, and all-arthroscopic cuff repair) vary, as each method provides an array of advantages and disadvantages.

The open surgical technique has long been considered the gold standard of rotator cuff repair, but surgeons are becoming more adept at decreasing patient morbidity through decreased surgical trauma from an all-arthroscopic approach.

Existing arthroscopic surgical techniques are based on sutures that are manually inserted (usually by a needle—either manually or mechanically) through the tendon on one end, and secured thereto, e.g., by binding, thereby allowing fixation of the tendon via said sutures to a standard bone anchor at the other end.

When choosing the precise location for the suture insertion at the tendon, the surgeon uses an arthroscopic grasper in order to pull the torn tendon toward the Humerus bone. This individual grasp does not provide the surgeon with the full pulling effect over the tendon's relocation, that the multi sutured tendon would experience at the end of the procedure. In a permanent grip made by a specific suture the forces are unbalanced and concentrated at the insertion point of each suture. Those unbalanced forces can cause an overload on a suture and can lead to suture failure or worst, unwanted suture dragging that may lead to additional tendon tear. Currently, the common failure in tendon-tear repairs happen in the interaction point between the stitching thread and the tendon, wherein re-tears occurring during early stage (first six months) represent a failure to heal. Accordingly, various surgical technique were developed to decrease re-tears: single row; double row; suture bridge; and knotless suture bridge.

There are currently several 'suture passer' devices which allow simultaneous suture passing and retrieval. Most of these devices reduce the procedure complexity, but require multiple repetitions, therefore do not shorten the procedures duration. Moreover, none of the known devices includes means for grasping the tendon in a balanced manner and/or relocating the sutures after securing same to the tendon.

The biomechanical construct (bone-tendon) has a critical effect on maintaining bone-tendon proximity to allow biologic healing, wherein current practice include usage of multiple suture anchors (between 1 to about 6).

Even with help of suture passers, the tendon's repair in today technologies requires a high expertise of the operating surgeon, and takes a long time. In addition, current procedures have many limitations: long immobilization period of about 2-6 weeks because of early re-tears; long rehabilitation, causing patients to avoid surgery; the tendon repair procedure is time consuming and requires multiple knots, sutures, and devices; and the procedures require a long learning curve for surgeons.

Accordingly, a need exists for an easy to use device and a simple method that enable better healing of a torn tendon, which are minimal invasive, enable to perform corrections and adjustments at any point throughout the surgical procedure, optionally cause minimal damage to the tendon, enables better healing that subsequently leads to shorter rehabilitation period, and may reduce the operation/procedure time. The present tendon repair device and method provide all of these and more.

SUMMARY OF INVENTION

The present invention provides a repair device 100 for a torn tissue, comprising: (a) a tissue attachment unit comprising (i) a tissue attachment element 111 comprising an attachment head 112; and (ii) an optional elongation tail 113; (b) a clamp unit 114 holding said tissue attachment element 111, comprising: (i) a base 115 acting as a positioning platform; (ii) side walls 116 securing the torn tissue in place and determining the attachment area; and (iii) a setter 117 holding the attachment element 111 and optionally sets the angle of its insertion into said tissue; and (c) binding means and/or an anchor associated with said elongation tail 113, if present.

The present invention further provides a torn tissue repair device 100 for re-attaching and securing a torn tissue in place or realigning torn edges back together, or connecting any two tissues, said device comprising: (a) a tissue attachment unit comprising (i) a tissue attachment element 111 comprising an attachment head 112 configured for securing said repair device 100 to said torn tissue, or realigning and fixing torn tissue edges back together, or connecting any two tissues; and (ii) an optional elongation tail 113; (b) a clamp unit 114 holding said tissue attachment element 111, comprising: (i) a base 115 acting as a positioning platform; (ii) side walls 116 securing the torn tissue in place and determining the attachment area; and (iii) a setter 117 holding the attachment element 111 and sets the angle of its insertion into the tissue; and (c) binding means and/or an anchor associated with said optional elongation tail 113 (or any other fixation site), wherein said torn tissue repair device 100, or at least said tissue attachment unit, are made-of a biocompatible and/or biodegradable and/or drug coated/releasing material(s).

The present invention further provides a method for repairing a torn tissue, said method comprising: (a) isolating said torn tissue; (b) selecting an attachment area ("preferred grip site") on said isolated tissue and securing same with the clamp unit 114 of a repair device 100 of the invention, wherein: the side walls 116 secure the torn tissue and outline the selected attachment area, while the base 115 serves as a tray on which said tissue lays; (c) reviewing the selected attachment area, and making adjustments in the attachment area if needed; (d) pressing the setter 117 of said clamp unit 114 holding an attachment head 112 to thereby secure said attachment head 112 to said torn tissue at said attachment area, wherein said pressing is carried out in a fixed movement, and wherein the base 115 of said clamp unit 114 provides a counter support when said setter 117 is pushed against the torn tissue; (e) if needed, lifting the setter 117 to extract said attachment head 112 from said tissue, adjusting the attachment area, and re-pressing the setter 117; (f) fastening the attachment unit, either via the elongation tail 113, if present, or directly to its target area; and (g) removing the clamp unit 114, leaving only the attachment element 111 secured to said tissue.

In specific embodiments, the tissue is a tendon.

BRIEF DESCRIPTION OF DRAWINGS

FIGS. 2A-2G illustrate five possible attachment heads/elements according to embodiments of the invention.

FIGS. 5A-5B illustrate two possible elongation tails according to certain embodiments of the invention: FIG. 5B—a flexible string-like tail enabling tying two tails together if needed. The tail may have zip tie/cable tie fixation element or based on mechanical ratchet.

DETAILED DESCRIPTION

The present invention provides an "all in one" device which helps the physician's actions become more accurate and less complicated to perform, giving the surgeon the ability to preview, grip, pull back and fix the tendon at a desired location in a simple procedure reducing procedure duration significantly.

Accordingly, the present invention provides a transformational technology for tendon-bone reattachment in the Rotator Cuff repair for achieving better healing and easier procedure. The present invention provides a minimally invasive, suture-less, single-handed, All-In-One gripping & reattaching system composed of an attachment element guided by a triple clamp device, which provides distributed forces for securing the tendon and maximizing contact area between tendon and bone and thus, allowing faster healing, earlier physical therapy and shorter rehabilitation period. In addition, the device of the invention is designed to reduce duration and complexity of current arthroscopic tendon repair surgeries.

The present invention provides a tendon attachment device for achieving better tendon-bone contact and balanced force distribution onto the attachment point to thereby reduce the risk of re-tear/detachment, allowing a preview of the selected attachment area, achieving a reliable anchoring of the tendon by a single insertion movement, and optionally while causing minimum damage to the tissue, and offering better tendon-bone contact area during the recovering time period. In certain embodiments, the procedure of attaching the tendon to the bone is reversible, thereby allowing improving/refining the contact between the tendon attachment device and the tendon during the attachment procedure. Moreover, the present method/technique may spare additional sewing, which is needed in vertical tendon tears. The device of the present invention by connecting to the torn tissue from only one side thereof without sandwiching the torn tissue, allows optimal tissue-tissue (e.g. tendon-bone) contact, which assists in reducing the healing time and/or reduces the risk of separation.

Accordingly, in a first embodiment, the present invention provides a repair device 100 for a torn tissue, comprising: (a) a tissue attachment unit comprising (i) a tissue attachment element 111 comprising an attachment head 112; and (ii) an optional elongation tail 113; (b) a clamp unit 114 holding said tissue attachment element 111, comprising: (i) a base 115 acting as a positioning platform; (ii) side walls 116 securing the torn tissue in place and determining the attachment area; and (iii) a setter 117 holding the attachment element 111 and optionally sets the angle of its insertion into said tissue; and (c) binding means and/or an anchor associated with said elongation tail 113, if present.

In certain embodiments of the repair device 100 of the invention, said attachment head 112 is configured for: (i) securing said repair device 100 to said torn tissue; (ii) realigning and fixing torn edges/tips of said torn tissue back together; and/or (iii) connecting any two tissues.

In certain embodiments, the repair device 100 of the invention, or at least said tissue attachment unit 111 is made of: a biocompatible material(s); and/or a biodegradable material(s).

In certain embodiments, the repair device 100 of the invention, or at least a part thereof comprises a drug releasing material(s).

Figure 5A:
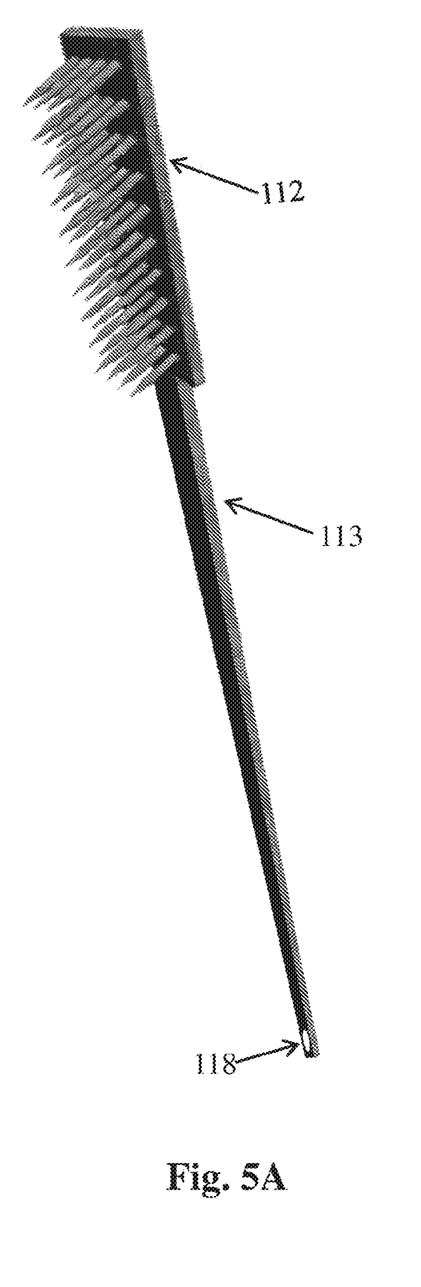
FIG. 5A—a rigid or flexible tail with an optional loop at its end (or several loops across to enable adjustment of the tail's length)
Figure 5B:
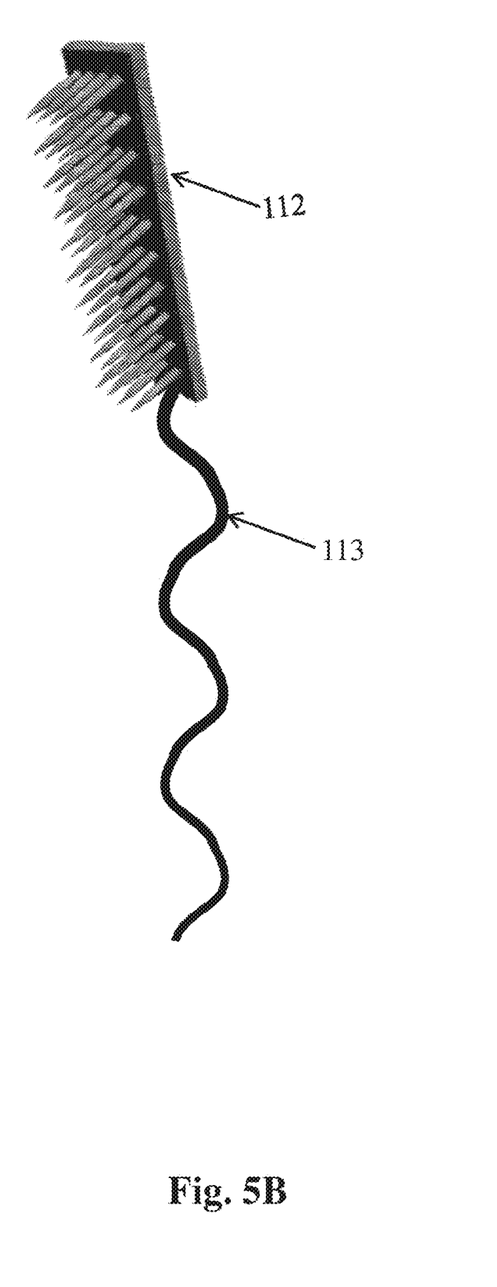

Accordingly, in other embodiments, the present invention provides a repair device 100 for faster re-attaching and securing a partial- or complete-torn tissue in place or realigning torn edges back together, or connecting any two tissues together, said device comprising (see FIGS. 1-4): (a) a tissue attachment unit comprising (i) a tissue attachment element 111 comprising an attachment head 112 configured for securing said repair device 100 to said torn tissue, or realigning and fixing torn edges/tips of said torn tissue back together, or connecting any two tissues, i.e. by binding/attaching to said torn tissue, e.g. using spikes, hooks, rough surface, etc., or any combination thereof; and (ii) an optional elongation tail 113 (FIGS. 5A and 5B) for aiding in securing/binding/attaching said tissue attachment element 111 to a desired target, e.g. a bone, another tissue, or another elongation tail 113 of a second repair device 100; (b) a clamp unit 114 holding said tissue attachment element 111, and optionally said elongation tail 113, for guiding said tissue attachment element 111 inside the patient's body, comprising: (i) a base 115 acting as a positioning platform; (ii) side walls 116 securing the torn tissue in place and determining the attachment area; and (iii) a setter 117 holding the attachment element 111 and optionally sets the angle of its insertion into the tissue; and (c) binding means and/or an anchor associated with said elongation tail 113 for securing said repair device 100 to a target area, e.g. a bone or a second repair device, wherein said repair device 100, or at least said tissue attachment unit 111, are made-of a biocompatible and/or biodegradable and/or drug coated/releasing material(s). In a specific embodiment, said tissue attachment unit 111 further comprises pharmaceutical compounds/compositions, optionally for slow drug release after installation in the patient's body, e.g. for reducing pain, facilitate healing and regrowth of the tissue.

In specific embodiments of the repair device 100 of the invention, said elongation tail 113 is absent.

In specific embodiments, the repair device 100 of the invention does not comprise said optional elongation tail 113, and the securing/binding/attaching of said tissue attachment element 111 to a desired target, e.g. a bone, another tissue, or a second repair device 100 or tail thereof, is carried out directly without it.

In a specific embodiment, said tissue is a tendon, and the device of the present invention is designed for repairing a torn tendon—at Grade I, II or even III. Accordingly, the present invention provides a torn tendon repair device 100 for fast re-attaching and securing a torn tendon in place or realigning torn edges back together, said device comprising: (a) a tendon attachment unit comprising (i) a tendon attachment element 111 comprising (i) an attachment head 112 configured for securing said repair device 100 to said torn tendon, or realigning and fixing torn tendon edges/tips back together, i.e. by binding/attaching to said torn tendon, e.g. using spikes, hooks, rough surface, etc., or any combination thereof; and (ii) an optional elongation tail 113 for aiding in securing/binding/attaching said tendon attachment element 111 to a desired target, e.g. a bone or another elongation tail 113 of a second repair device 100; (b) a clamp unit 114 holding said tendon attachment element 111, and optionally said elongation tail 113, for guiding said tendon attachment element 111 inside the patient's body, comprising: (i) a base 115 acting as a positioning platform; (ii) side walls 116 securing the torn tendon in place and determining the attachment area; and (iii) a setter 117 holding the attachment element 111 and optionally sets the angle of its insertion into the tendon; (c) binding means and/or an anchor associated with said elongation tail 113 for securing said repair device 100 to a target area/site, e.g. a bone or a second repair device, wherein said torn tendon repair device 100, or at least said tendon attachment unit 111, are made-of a biocompatible and/or biodegradable and/or drug coated/releasing material(s).

Figure 1A:
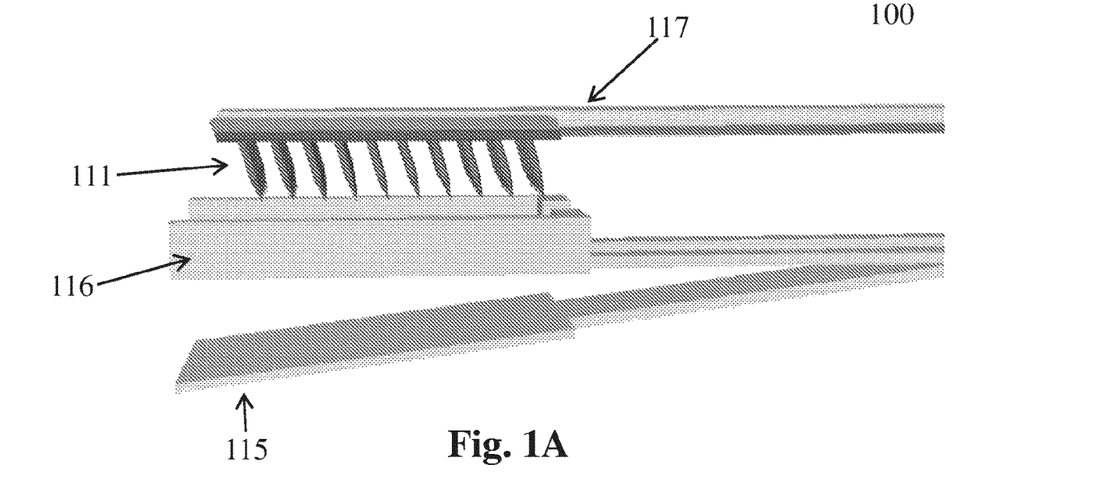
FIGS. 1A-1B are a 3-dimensional illustration of the tendon repair device of the invention.
Figure 1B:
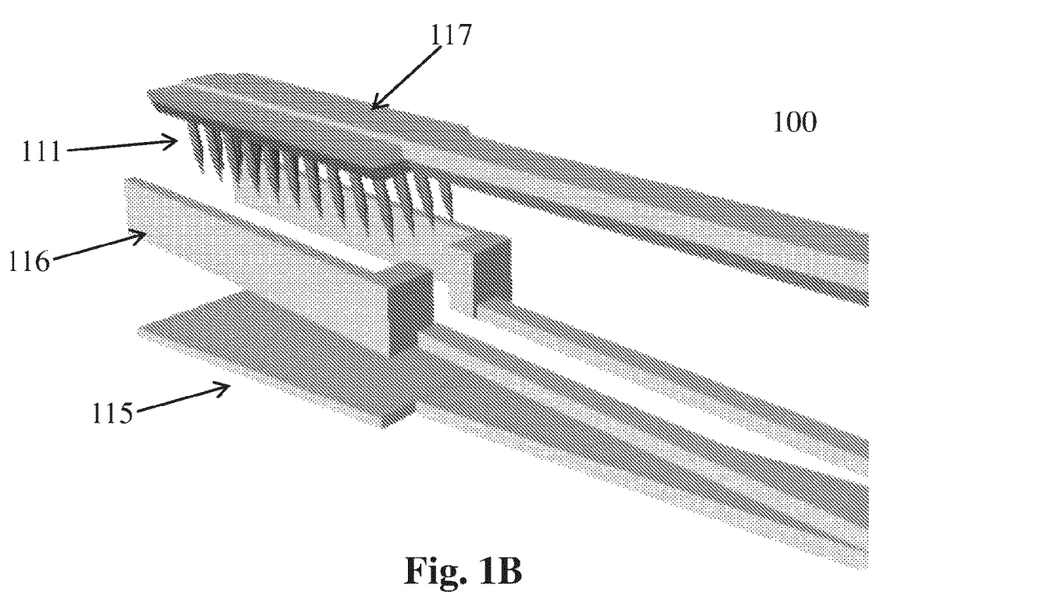
Figure 2A:
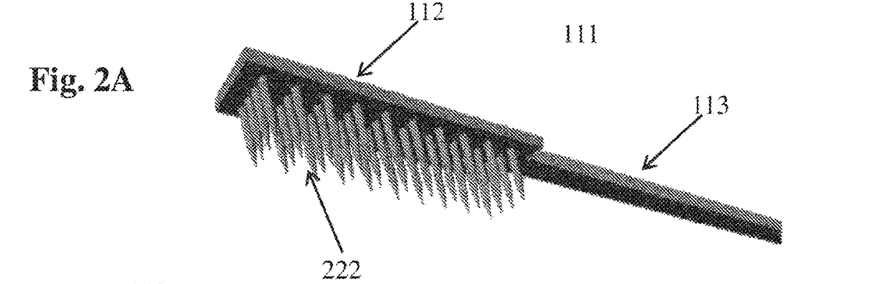
FIG. 2A shows a standard attachment head with several columns of even-sized angled spikes.
Figure 2B:
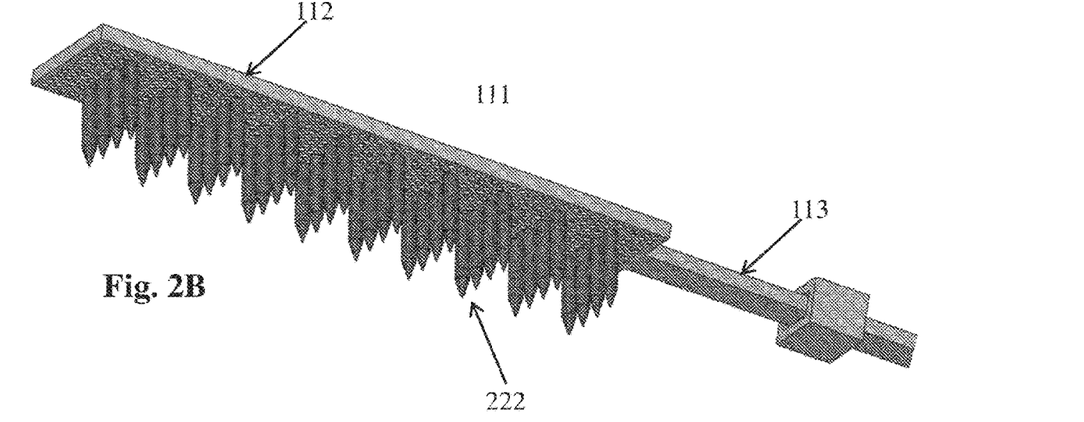
FIGS. 2B-2C show a perforated attachment head enabling tissue growth therein.
Figure 2C:
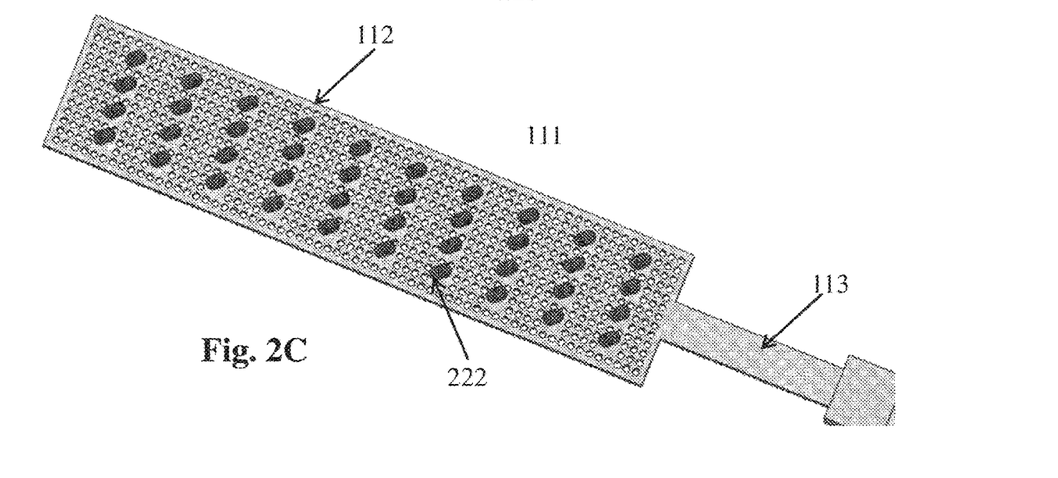
Figure 2D:
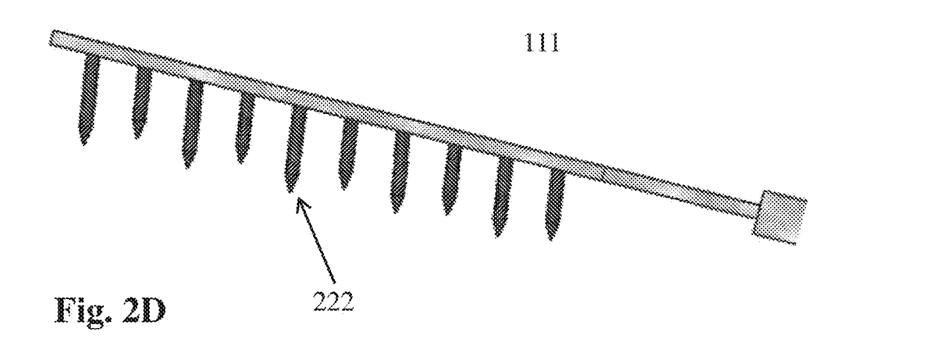
FIG. 2D shows an attachment head with several columns of spikes, each of a different length.
Figure 2E:
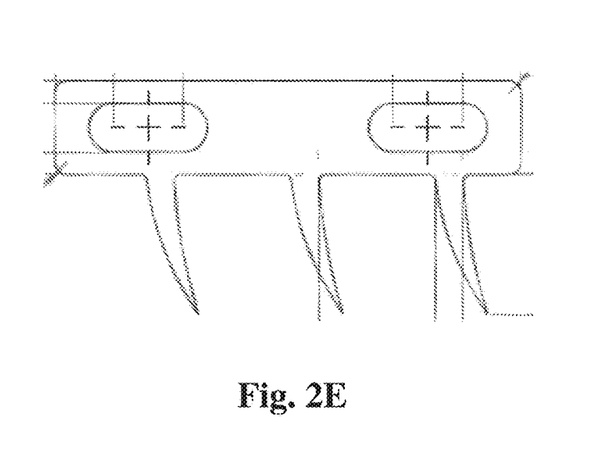
FIGS. 2E-2F show attachment head No. MP0038 with a 5-column of even-length curved spikes.
Figure 2F:
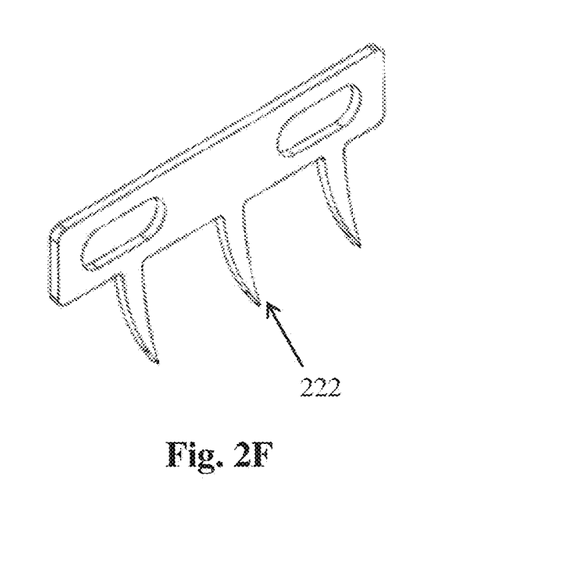
Figure 2G:
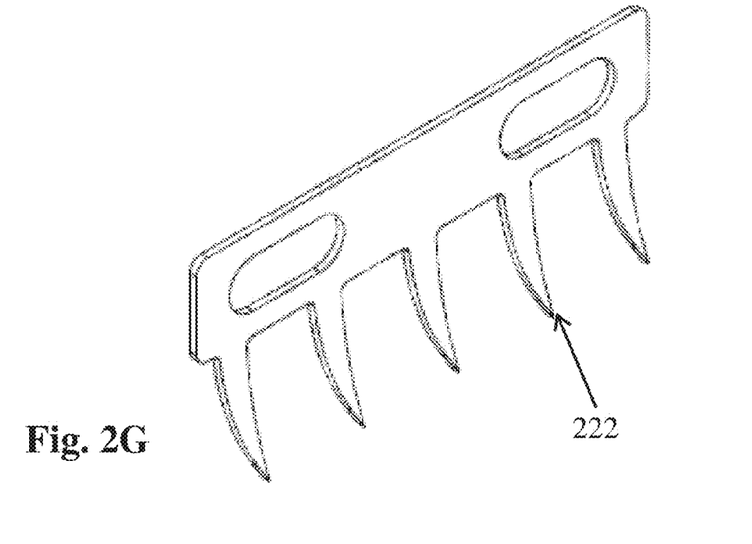
FIG. 2G shows attachment head No MP0033 with a 3-column of even-length curved spikes.
Figure 3:
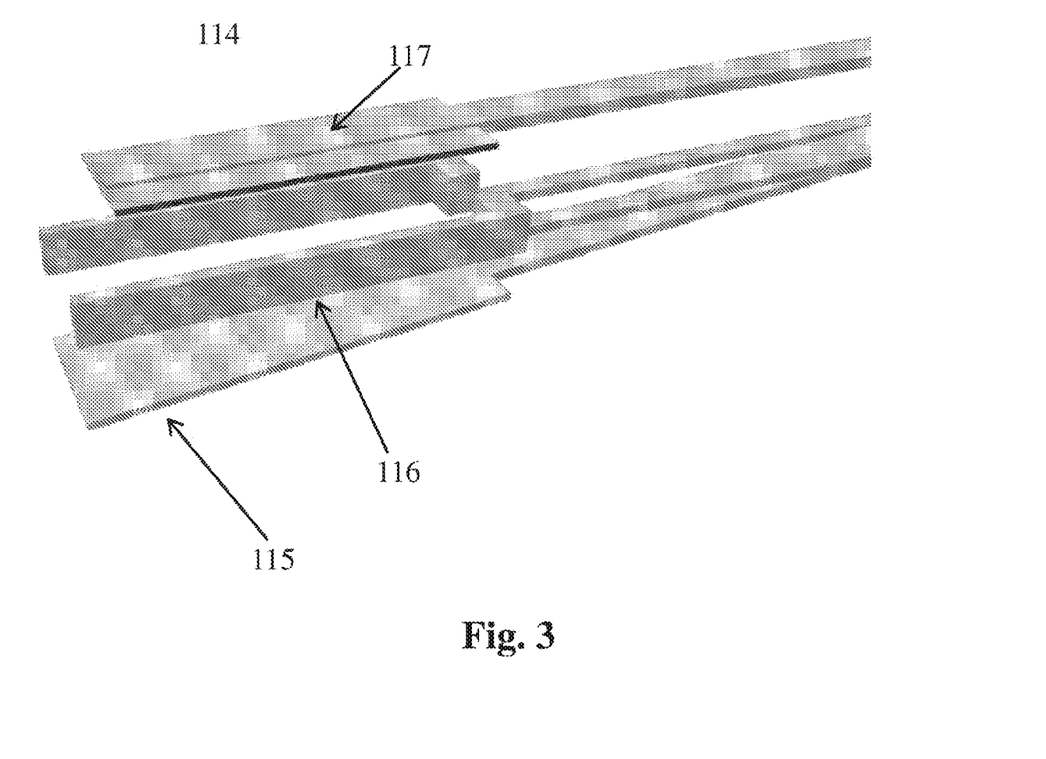
FIG. 3 illustrates the clamp unit according to the invention.
Figure 4:
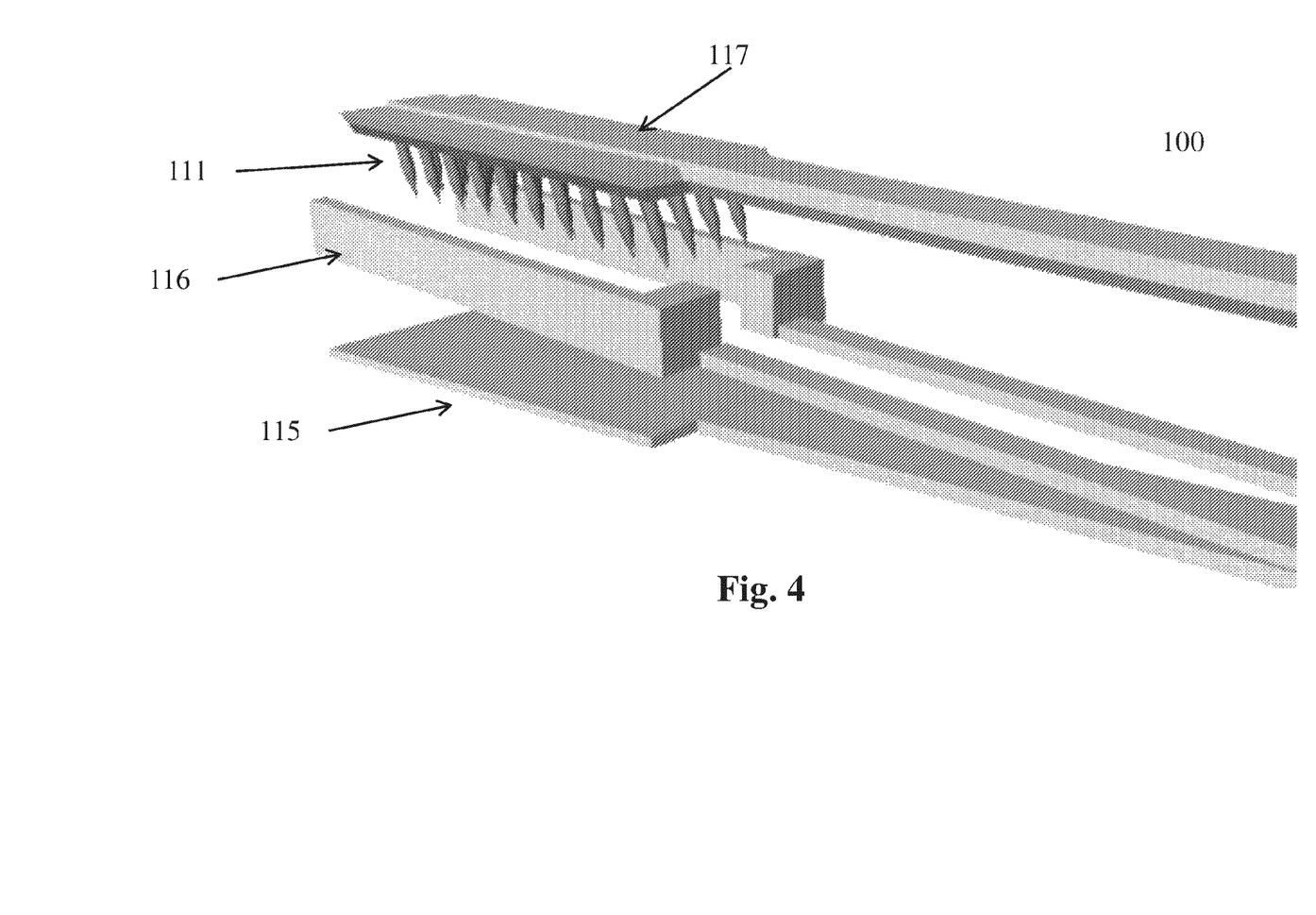
FIG. 4 illustrates the full kit device—a combination of the attachment element as illustrated in FIG. 2A with the clamp unit as illustrated in FIG. 3.

In certain embodiments, said spikes may be cutout from the surface and bend to their final shape, i.e. constituting an inherent part originating from the same "sheet"/"block" of material (see e.g. FIGS. 2E-2G). Alternatively, the spikes can originate from several individual elongated elements as separated rows of spikes, inserted into a platform and tightened/secured together in their final configuration (see e.g. FIGS. 2A-2D). In both options, empty spaces are formed between the spikes, enabling the regeneration of the tissue/tendon to thereby incorporate into the attachment element. In certain embodiments, the spikes are differential: in length, in dispersion across the attachment head, and/or in diameter. They may even be differential for different patients. This differentially improve securing of said attachment unit to said torn tissue/tendon In certain embodiments, the attachment head 112 is rigid. In alternative embodiments, the attachment head 112 is somewhat flexible or semi-rigid, while the spikes are rigid. In yet other embodiments, the attachment head 112 is made of a solid plate. In alternate embodiments, the attachment head 112 is constructed as a perforated or mesh-like plate, wherein the size of the holes is either fixed or differential. In specific embodiments, the spikes are perforated. Such perforation or mesh-like structure enables tissue to grow into the cavities to thereby strengthen the binding of the attachment head 112 to the tissue.

Notably, when referring to the attachment of said attachment head 112 to the torn tendon/tissue, it may be attached either only to the torn tendon/tissue tip, to the whole tendon/tissue area, or to any other part/area of the torn tendon/tissue.

In certain embodiments of the repair device 100 of the invention, said tendon/tissue attachment unit 111 is made-of, or comprises of biocompatible and/or biodegradable and/or drug coated/releasing materials. Non-limiting examples of such materials are: metals and their alloys; polymers and co-polymers (including bioactive/biodegradable polymers/co-polymers); ceramics; or any combination thereof. In specific embodiments, said tendon/tissue attachment unit 111 may be constructed/manufactured by using powder metallurgy technology, or any other similar technology, to produce controlled porous structures that allow the tissue/tendon ingrowth within the implanted surface, thereby improving fixation of the device into the tissue/tendon. In another specific embodiment, said tendon/tissue attachment unit 111 is further coated with supplementary materials, such as drug releasing materials, immune-suppressing materials, hormones, tissue-generating materials, etc. for assisting in tissue/tendon repair and fusion with the tendon/tissue attachment unit 111 and/or the target area/site or other part of the torn tissue/tendon.

In specific embodiments, the repair device 100 of the invention or some of its components, undergo further processing, such as vibration finish, in order to smoothen sharp edges thereof, to thereby reduce/eliminate possible damage to surrounding tissues during insertion of the device into the patient's body.

In certain embodiments of the repair device 100 of the invention, said attachment head 112 comprises spikes, hooks or rough surface(s), or any combination thereof configured for attaching to said torn tendon/tissue. In specific embodiments, the size, length, shape and angle of said spikes and hooks may be differential along the attachment head 112 or even for different patients, to thereby improve securing of said attachment unit to said torn tissue/tendon. In a specific embodiment, said attachment head 112 and/or said spikes and hooks are designed such that they enable growth of a biological tissue therewithin, e.g. by being hollow, comprise cavities, or having a mesh/net structure.

In certain embodiments of the repair device 100 of the invention, said attachment head 112: (i) has a perforated structure for allowing tissue to grow therewithin; (ii) is made of bio-degradable and/or bio-compatible material; (iii) is coated, e.g. with drug releasing capabilities, healing/regeneration-mediated substances, immunodepression material(s), growth factors, stem cells, anti-inflammatory, and/or any other drug and/or any chemical/biological matter or combination that improves healing; (iv) is costume made according to patient's/tissue's anatomy and/or the tissue being repaired; and/or (v) is perforated or net-like structured.

In yet another specific embodiment, said attachment head 112 comprises spikes and/or hooks, and distribute the pulling force applied onto the attached tissue/tendon between all of said spikes and/or hooks, thereby reducing the risk of damage to the tissue/tendon and/or the risk of tearing/ripping the attachment element 111 off of the tissue/tendon. This is achieved by providing an individual gripping point between each of said spikes or hooks in said attachment head 112 and said tissue/tendon, thereby distributing the pulling force applied on the tissue/tendon between all of said gripping points.

In yet another specific embodiment, said attachment head 112 comprises spikes, and is designed such that said spikes can be inserted into said torn tendon at a predefined angle (this happens when the angle of the spikes/hooks have the same angle as the setter 117), removed/extracted-therefrom if needed, e.g. to fix or adjust the binding of the repair device 100 to the torn tissue/tendon, minimizing any additional damage to the tissue/tendon, and subsequently reinserted into said torn tissue/tendon. The movement of the insertion may also be radial, originating from an axis at the distal part of the head's surface—accordingly, the spikes in such a case would be rounded.

In certain embodiments of the repair device 100 of the invention, said spikes are: (i) differential, personalized and/or perforated; and/or (ii) foldable and/or extractable.

In specific embodiments, the insertion of the attachment head 112 into the patient's body is carried out while the attachment head is in a folded form, e.g. when the spikes, hooks, rough surface, etc. are folded or concealed. In this configuration, the spikes, hooks, rough surface, etc. are exposed or pup-out when the attachment head 112 is positioned in close proximity to the attachment area. This reduces the risk of potential damage to tissues during the insertion of the device into the patient's body.

In certain embodiments, the attachment head 112 is constructed in any shape and size. For instance, it can have a rectangle-, oval-, square-shape, having a width of from about 1 to about 100 mm, and a length of from about 1 to about 100 mm. It should be noted that the shape and size of the attachment head 112 is determined according to the specific tissue/tendon being repaired and said tissue/tendon individual characteristics. Accordingly, in certain embodiments, the size and shape of the attachment head and/or the spikes are determined according to the specific patient being treated, the tissue type, the type of damage/rupture, and patent's/tissue's specific anatomy, or any combination thereof.

In certain embodiments, the length of the elongation tail 113 can be adjusted on site as needed, e.g. by cutting it short, and/or by adding or removing threads to adjust its thickness and/or length. It should be noted that the length and width of the elongation tail 113 is determined according to the specific tissue/tendon being repaired, its distance from the anchoring target, point of tear, etc.

In certain embodiments of the repair device 100 of the invention, said anchor is present, and configured to secure said attachment element 111, optionally via said elongation tail 113, to a bone or to any other tissue, or to another device, e.g. with screw, adhesive, ratchet mechanism, pressure fixation mechanism, cable tie mechanism, tying a knot, etc. Alternatively, said anchor is absent, and said attachment element 111, optionally via said elongation tail 113, is attached to a second attachment element or any other device, optionally via its elongation tail 113, e.g. by tying or binding said two tails together, via a loop 118 (FIG. 5A), or via any other connection unit.

In another embodiment of the repair device 100 of the invention, said elongation tail 113 is absent, and said attachment element 111 is secured in place via a direct connection to the anchoring site, e.g. through a drill hole at the attachment head 112. Alternatively, said elongation tail 113 is present, and is used to secure said attachment element 111 to the anchoring site.

In another embodiment of the repair device 100 of the invention, said clamp unit 114 defines a tissue/tendon-attachment area at said torn tissue/tendon to which said attachment head 112 binds.

According to some embodiments of the invention, the number of spikes in the repair device 100 of the invention may vary according to the mechanical properties of the tissue involved, as well as the tissue dimensions. For instance, soft tissue will require less spikes, whereas hard/compact or stiff material would probably require a larger number of spikes. Similarly, large tissue would require a larger number of spikes compared to a smaller tissue. Accordingly, in some embodiments of the invention, the repair device 100 of the invention may comprise from 1 to 1000; from 2 to 750; from 3 to 500; from 4 to 400; from 5 to 300; from 5 to 250; from 5 to 200; from 5 to 150; from 5 to 100; from 7 to 100; from 8 to 100; from 9 to 100; from 10 to 100; or from 10 to 50 spikes/hooks.

In other embodiments, the number of spikes/hooks rows and/or columns is from 1 to 10,000; from 1 to 5,000; from 1 to 1,000; from 1 to 500; from 1 to 250; from 1 to 100; from 1 to 50; from 1 to 25; from 2 to 25; from 3 to 25; from 4 to 25; from 5 to 25; from 7 to 25; or from 10 to 25. And the distance between two adjacent spikes/hooks is from 1 µm to 30 mm; from 1 µm to 25 mm; from 1 µm to 20 mm; from 1 µm to 15 mm; from 1 µm to 10 mm; from 1 µm to 5 mm; from 2 µm to 30 mm; from 3 µm to 30 mm; from 4 µm to 30 mm; from 5 µm to 30 mm; from 5 µm to 20 mm; from 5 µm to 10 mm; from 5 µm to 5 mm; from 5 µm to 1 mm; or from 5 µm to 0.1 mm.

In other embodiments, the length of said spikes/hooks is from 1 µm to 30 mm; from 1 µm to 25 mm; from 1 µm to 20 mm; from 1 µm to 15 mm; from 1 µm to 10 mm; from 1 µm to 5 mm; from 2 µm to 30 mm; from 3 µm to 30 mm; from 4 µm to 30 mm; from 5 µm to 30 mm; from 5 µm to 20 mm; from 5 µm to 10 mm; from 5 µm to 5 mm; from 5 µm to 1 mm; or from 5 µm to 0.1 mm.

In another embodiment, the thickness of said spikes/hooks is from 1 µm to 10 mm; from 1 µm to 7.5 mm; from 1 µm to 5 mm; from 1 µm to 2.5 mm; from 1 µm to 1 mm; from 1 µm to 0.5 mm; from 2 µm to 10 mm; from 3 µm to 10 mm; from 4 µm to 10 mm; from 5 µm to 10 mm; from 5 µm to 5 mm; from 5 µm to 1 mm; from 5 µm to 0.5 mm; from 5 µm to 0.1 mm; or from 5 µm to 0.05 mm.

In specific embodiments, said spikes/hooks are in an upright position, i.e. have an angle of 90° to their base. Alternatively, they may be in any desired angle relative to their base, e.g., from 10°-100° from 1° to 179°; from 5° to 170°; from 10° to 160°; from 15° to 150°; from 20° to 140°; from 30° to 130°; from 40° to 120; from 50° to 110; from 60° to 100; from 70° to 100; or from 80° to 100°. In some embodiments, the spikes are shaped according to the designated insertion movement pathway. Accordingly, the angle or curve of the spikes will correspond to the element most suitable for each use: for instance, the movement of the setter 117 can be used as the guide, or alternatively, the movement of the side walls 116. For example, if the spikes are at a certain angle, an additional part that will close the side walls 116 to a full rectangular frame can be tilted to the same angle of the spikes, thereby helping in the guidance of the spikes by this geometric support. Alternatively, if the spikes are curved, a circular movement around the axis during the movement of the setter 117 may be used as guidance means.

In certain embodiments of the repair device 100 of the invention, said side walls 116 further comprise a mechanical element, such as a hinge- or roller-like, that assists in spreading, stretching and/or straightening the tissue for attaching said tissue attachment unit thereto.

In certain embodiments, the length of the attachment head 112, the base 115, the side walls 116 and the setter 117, is the same or different, and is from 0.1 mm to 100 mm; from 0.1 mm to 90 mm; from 0.1 mm to 80 mm; from 0.1 mm to 70 mm; from 0.1 mm to 60 mm; from 0.1 mm to 50 mm; from 0.1 mm to 40 mm; from 0.5 mm to 100 mm; from 1 mm to 100 mm; from 2.5 mm to 100 mm; from 5 mm to 100 mm; from 10 mm to 100 mm; from 20 mm to 100 mm; from 1 mm to 50 mm; from 2.5 mm to 50 mm; or from 5 mm to 50 mm And their width and thickness is the same or different, and is from 0.1 mm to 50 mm; from 0.1 mm to 45 mm; from 0.1 mm to 40 mm; from 0.1 mm to 35 mm; from 0.1 mm to 30 mm; from 0.1 mm to 25 mm; from 0.1 mm to 20 mm; from 0.5 mm to 50 mm; from 1 mm to 50 mm; from 2.5 mm to 50 mm; from 5 mm to 50 mm; from 10 mm to 50 mm; from 20 mm to 50 mm; from 1 mm to 35 mm; from 2.5 mm to 35 mm; from 5 mm to 35 mm; or from 5 mm to 70 mm.

In certain embodiments, the length of the elongation tail 113, if present, is adjustable according to need, and may be from 0.1 mm to 250 mm; from 0.1 mm to 200 mm; from 0.1 mm to 150 mm; from 0.1 mm to 100 mm; from 0.1 mm to 50 mm; from 1 mm to 200 mm; from 5 mm to 200 mm; from 10 mm to 200 mm; from 15 mm to 200 mm; from 25 mm to 200 mm; or from 50 mm to 200 mm.

In certain embodiments, the spikes can be immersed in a pharmacological agent/therapeutic agent/stem cells, or any other material, composition or agent, to facilitate faster healing of the tissue and/or to strengthen the binding/association of the repair device 100 with the tissue, thereby increasing the effectiveness of said repair device 100.

The above specified parameters are in accordance with the various tissues and tendons that can be repaired with the repair device 100 and method of the invention. Accordingly, when attempting to fix/repair an arm tendon, a different repair device may be used compared to that used for fixing a leg tendon. Similarly, a different repair device may be used in a child compared to that used for fixing the same tissue/tendon in an adult.

In other embodiments, the repair device 100 of the invention further comprises at least one of: an optic fiber, an illumination unit, forceps or any other grasping means, electromagnet, springs, pressure sensors, tension sensors, tendon conveyor belt, or any other component that might be of use during surgery, or any combination thereof.

In yet another embodiment, the repair device 100 of the invention further comprises: (i) at least one more attachment head, thereby enabling securing of the tissue/tendon from multiple angles and directions; and/or (ii) a folding-, opening- and/or extractable-attachment head.

According to the present invention, when performing any medical tendon repair procedure (FIG. 7A), the surgeon selects the preferred tendon grip site, temporarily secures it using the clamp's middle (side walls 116) and lower (base 115) parts, i.e. by applying moderate pressure on the tendon's superior and inferior surfaces, thereby preventing it from moving: (i) the clamp's base 115 serves as a tray the tendon lays on, and provides the counter support (dotted arrow) needed when inserting the spikes/hooks of the attachment element 111 into the torn tendon; (ii) the clamp's side walls 116 secure the tendon and outline the selected attachment area. Additionally, cog wheels (or any other rolling element) may be installed on each side of the above-mentioned components, thereby enabling controlling their movements (optionally manually) and help stretching the tissue to achieve the tension required in order to insert the spikes successfully.

Figure 7A:
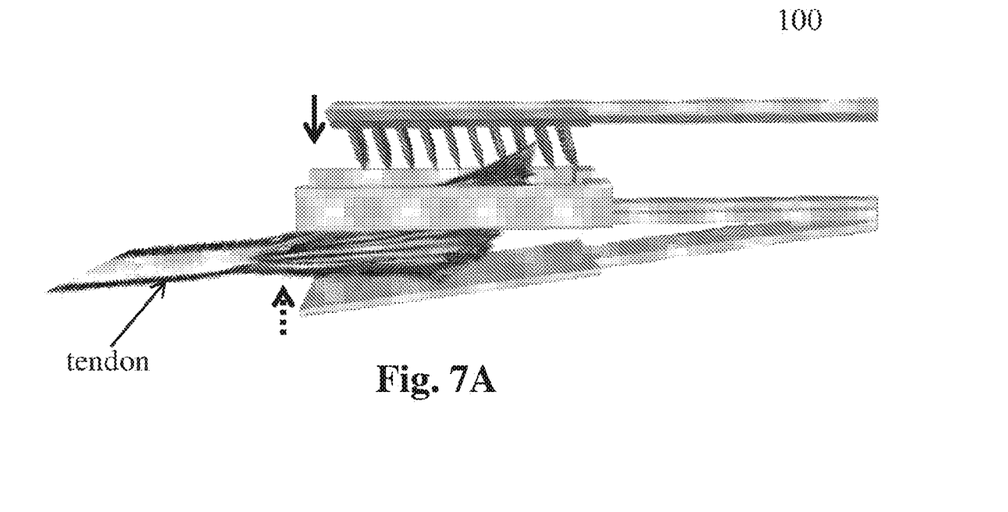
FIGS. 7A-7B illustrate how the repair device of the invention is attached to the torn tip of a Grade 3 torn tendon (complete torn tendon).
Figure 7B:
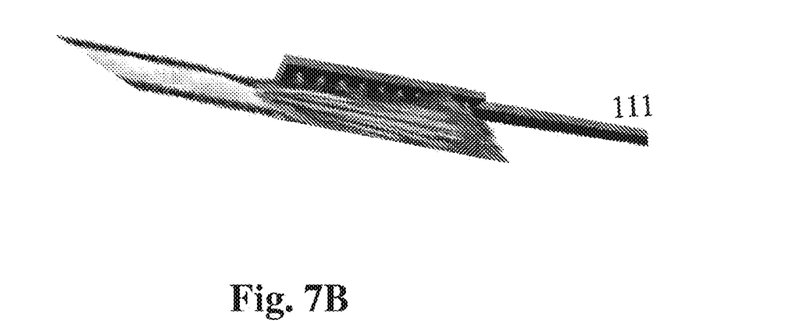

Then, the surgeon gets a preview of the designated attachment area being held by the clamp, e.g., through a hollow outline therein or an optic fiber, thereby enabling the surgeon to make adjustments in the attachment area if needed. This feature enables the alignment of the tears' edges and joins them in a single outline defined attachment area (FIG. 7), thereby renders the currently mandatory sewing of vertical tears before it is possible to reattach a torn tendon to a bone, redundant.

The clamp's upper part (setter 117), which holds the attachment element 111 (e.g. by a reversible locking system that can hold the two together, release said attachment element 111 when needed, and reconnect and hold it again if a mistake had been made and the element needs to be pulled out), inserts the spikes/hooks of the attachment element 111 into the tendon, in a fixed movement according to the spikes' shape/angle/radius. The fixed movement guides the spikes into the tendon. In certain embodiments, the force used for the insertion of the spikes into the tendon is implied by any suitable mechanism, such as, but not limited to, a spring, a hydraulic mechanism or electromagnetism. The tendon holding and inserting mechanism according to the invention enables a fast and minimal force application during penetration of the attachment element's spikes to the tendon, by simply applying suitable pressure between the base 115 and the setter 117 when a tendon is fixed there between.

In certain embodiments, the repair device 100 further comprises a vibrating element or a vibration-generating unit, in order to facilitate penetration of the spikes into the tissue, and/or to improve the binding and association of the repair device 100 with the tissue, i.e. by vibrating the tissue which may speed up its healing around the spikes. Alternatively, such a vibrating element or a vibration-generating unit may be used to re-position the spikes in the repaired tendon/tissue.

Figure 6:
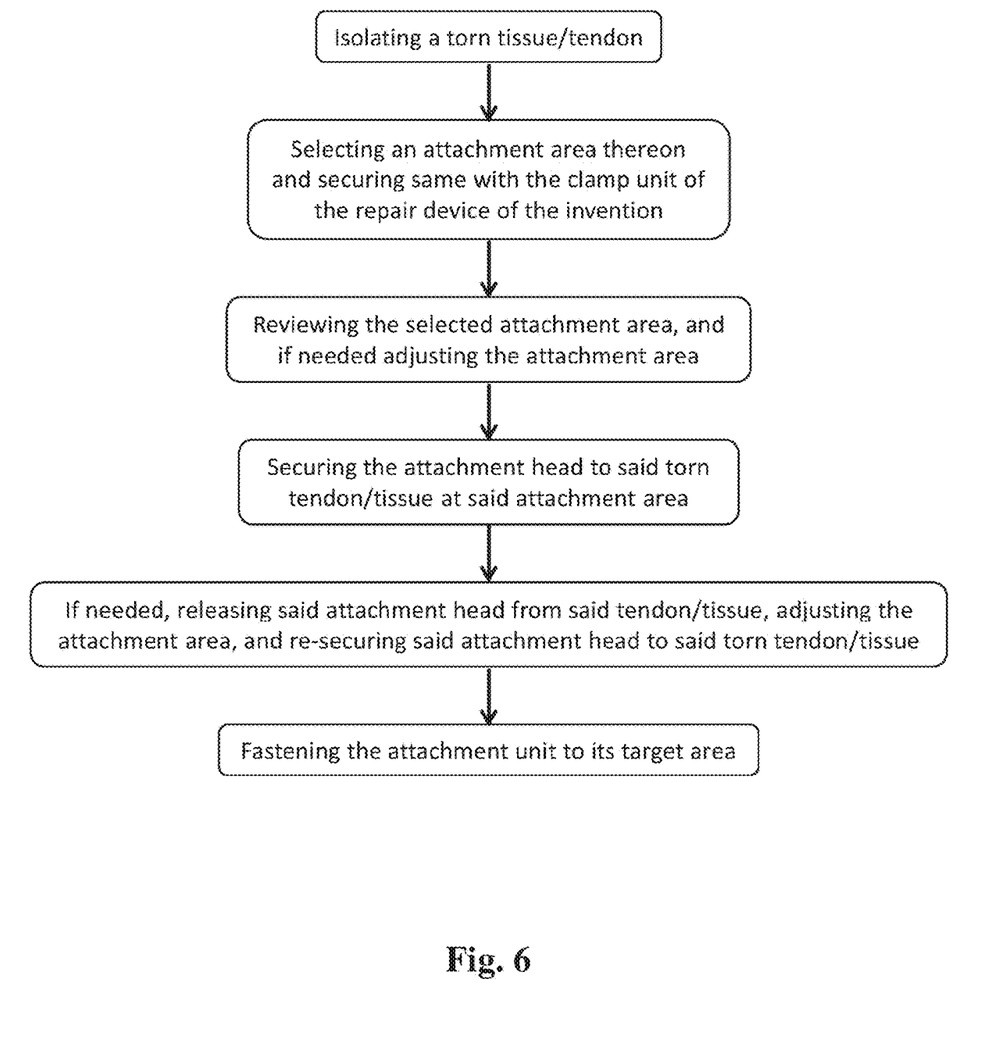
FIG. 6 is a block diagram illustrating how to use the tendon repair device of the invention.

Accordingly, in another embodiment, the present invention provides a method for fast repairing a torn tissue (see e.g. FIG. 6), said method comprising: (a) isolating said torn tissue, i.e. the longer torn section, or both torn sections of said tissue; (b) selecting an attachment area ("preferred grip site") on said isolated tissue and securing same with the clamp unit 114 of a repair device 100 according to the invention, wherein: the side walls 116 secure the torn tissue and outline the selected attachment area, while the base 115 serves as a tray on which said tissue lays; (c) reviewing the selected attachment area, and making adjustments in the attachment area if needed; (d) pressing the setter 117 of said clamp unit 114 holding an attachment head 112 to thereby secure said attachment head 112 to said torn tissue at said attachment area, wherein said pressing is carried out in a fixed movement according to the spikes/hooks shape, angle and size, wherein such a fixed movement guides the spikes/hooks into the tissue, and enables extraction of such spikes if needed, e.g. for re-adjustments, and wherein the base 115 of said clamp unit 114 provides a counter support when said setter 117 is pushed against the torn tissue; (e) if needed, lifting the setter 117 to extract/release said attachment head 112 from said tissue, adjusting the attachment area, and re-pressing the setter 117; (f) fastening the attachment unit, either via the elongation tail 113, if present, or directly to its target area, e.g. a bone, the other part of the torn tissue, or any other tissue, or an elongation tail of another repair device; and (g) removing the clamp unit 114, leaving only the attachment element 111 secured to said tissue from only one side thereof thereby avoiding sandwiching of the torn tissue when held thereby (FIG. 7B).

In a specific embodiment, the tissue is a tendon and tendon repair method comprises the steps of: (i) selecting the preferred tendon grip site using the attachment element; (ii) inserting the attachment element into the tendon by the clamp's upper part; (iii) in case of miss-positioning, removing the attachment element in a 'reverse fixed movement'; and (iv) fastening the attachment element's strap to a standard knotless anchor in the Humerus bone and clamp's removal.

In a specific embodiment, the tissue is a tendon and the present invention provides a method for fast repairing a torn tendon (see e.g. FIG. 6), said method comprising: (a) isolating said torn tendon, i.e. the longer torn section, or both torn sections of said tendon; (b) selecting an attachment area ("preferred grip site") on said isolated tendon and securing same with the clamp unit 114 of a repair device 100 according to the invention, wherein: the side walls 116 secure the torn tendon and outline the selected attachment area, while the base 115 serves as a tray on which said tendon lays; (c) reviewing the selected attachment area, and making adjustments in the attachment area if needed; (d) pressing the setter 117 of said clamp unit 114 holding an attachment head 112 to thereby secure said attachment head 112 to said torn tendon at said attachment area, wherein said pressing is carried out in a fixed movement according to the spikes/hooks shape, angle and size, wherein such a fixed movement guides the spikes/hooks into the tendon while causing minimum damage thereto, and enables extraction of such spikes if needed, e.g. for re-adjustments, and wherein the base 115 of said clamp unit 114 provides a counter support when said setter 117 is pushed against the torn tendon; (e) if needed, lifting the setter 117 to extract/release said attachment head 112 from said tendon, adjusting the attachment area, and re-pressing the setter 117; (f) fastening the attachment unit, either via the elongation tail 113, if present, or directly to its target area, e.g. a bone or any other tissue, or an elongation tail of another repair device; and (g) removing the clamp unit 114, leaving only the attachment element 111 secured to said tendon (FIG. 7B).

In certain embodiments of the method according to the invention, said setter 117 in step (d) participates in the actual pushing of the spikes/hooks of the attachment head 112 into the tendon or tissue.

In certain embodiments of the method according to the invention, the repair device 100 of the invention can be adjusted/constructed to connect any two tissues-either two sections of the same tissue (e.g. tendon-to-tendon or muscle-to-muscle), or two different tissues (e.g. tendon-to-muscle or tendon-to-bone).

In certain embodiments of the method of the invention, the attachment element 111 of the repair device 100 can be inserted into the patient's body during any surgical type, e.g. "open" surgery, arthroscopic surgery or any other endoscopic surgery. In specific embodiments, the attachment element 111 can be inserted unto the patient's body either in an "open" form, or in a folded form, in which case the spikes/hooks are folded or not exposed during insertion, but are spread/brought into an upright position to its final open operational geometry only inside the body at the desired assembly/attachment point.

In certain embodiments of the method according to the invention, step (e) is performed after step (f) or after step (g), i.e. by re-connecting the clamp unit 114 to said attachment element 111.

In certain embodiments, after attaching the repair device 100 of the invention to the torn tendon/tissue, the tendon/tissue and the repair device 100 are held together by the tension forces applied by the tendon/tissue when it pulls toward one direction, while the attachment element 111 once secured in place (e.g. via the elongation tail 113), provides a counter pull to the other direction. For instance, when the device 100 is attached to a torn tendon, the tendon pulls towards one direction whereas the device, which is secured, e.g., to a bone provides a counter pull to the other direction. These counter forces create a continuous pressure applied onto the hooks/spikes embedded within said tendon and prevents their unintentional/undesired departure.

In certain embodiments, the method according to the invention further comprises a step of attaching another (e.g. secondary) attachment head to another location and/or direction at said attachment area or another nearby attachment area, wherein said attachment head is either an attachment head 112 of another repair device 100 (which is attached to the tissue/tendon after attaching the first attachment head 112), or a secondary attachment head present in the same repair device 100.

In another embodiment of the method of the invention, if and when needed, e.g. for tendons, tissues or areas that are susceptible to reverse movement which might release the attachment head 112 from the tendon/tissue, the surgeon may further attach to the torn tendon/tissue a secondary attachment head, optionally with spikes or hooks positioned in an angle opposite to that of the original attachment head 112, thus providing additional fixing of the tendon/tissue, and enabling an increased attachment and fastening of the repair device 100 to the torn tendon/tissue, and avoiding undesired release due to such revers movement. Accordingly, in certain embodiments, the repair device 100 of the invention further comprises 1, 2, or 3 secondary attachment heads located, e.g., at the base 115 or at any of the side walls 116, or any combination thereof.

The absence of sutures between the tendon and the bone leaves the contact area to be maximal, and prevents physical interference of the sutures. Additionally, the sutures in existing methods tend to create air holes due to creating geometric distortion at the tendon. On the other hand, the present device and kit 100 with its spread spikes reduces those distortions while creating a better contact area with the tendon.

In certain embodiments, in case of a mistake, i.e. when the device attachment element 111 is attached at/in a wrong position onto the torn tendon, a "reverse fixed movement" of the setter 117 can extract the spikes out of the tendon as the attachment element 111 is removed—with very little, if at all, additional harm to the tissue. Accordingly, said setter 117 enables a "revers movement", i.e. extraction of the spikes of the attachment element 111, for undoing the spikes' insertion. Thus, in certain embodiments, the setter 117 serves as the both an insertion/removal guide as well as a pressing mechanism. In yet another embodiment, the attachment element 111 can reconnect to said setter 117 also after it has already been released, e.g. when there is a need to amend/adjust the attachment of the device to the tendon.

After securing the attachment element 111 to the tendon, the surgeon fastens the attachment element to its designated target and removes the clamp unit 114, leaving only the attachment element 111 to hold the tendon, pull it and press it towards the designated anchoring tissue (e.g. a bone). In a specific embodiment, this is carried out by passing the elongation tail 113 through an anchor drilled in the humerus bone.

The entire procedure according to the invention should take much less operation time compared to known techniques currently being used, e.g. twice as fast, 3-times or even 4-times faster. In a specific embodiment, the procedure shall not take more than 20 minutes.

In specific embodiment, the repair device 100 of the invention could be a fully- or partially-electromechanical device, and not only mechanical, and its installation may be controlled or completely performed (such as robotic operation) by, e.g., a computer.

The devices and methods according to the present invention enable the user to achieve a reliable hold of the tendon by only one insertion movement, while penetrating the tissue/tendon in multiple points simultaneously. As such, the present invention provides many advantages over those of the prior art: faster and easier "all in one" tool which helps the surgeon's actions become more accurate and less complicated to perform, giving the surgeon the ability to preview, grip, pull back and fixate the tendon at a desired location in a simple procedure; allowing a preview of the attachment area selected by the surgeon; sparing additional sewing needed in vertical tears by including the entire vertical tear in the preview area; reducing re-tear rate by using balanced force distribution; and allowing optimal tendon-bone contact area that is required for better and shorter healing period.

EXAMPLES

Example 1

Development and Production of Preliminary Attachment Element Prototypes

Ex-Vivo experiments were performed with a variety of attachment elements geometrical configuration: 14 different attachment elements were tested for load to failure tensile test between the attachment element and a pig's Supraspinatus tendon using an Instron machine. Results are shown in Table 1 below:

TABLE 1

| Test No. | Model number | Surface thickness [mm] | Number of columns | Number of spikes per column | Spikes length | Load to failure [N] |
|---|---|---|---|---|---|---|
| 1 | MP0032 | 0.3 | 3 | 6 | 2.5 | 72 |
| 2 | MP0032 | 0.3 | 3 | 6 | 2.5 | 15 |
| 3 | MP0032 | 0.3 | 3 | 6 | 2.5 | 42 |
| 4 | MP0037 | 0.1 | 2 | 8 | 6 | 49 |
| 5 | MP0038 | 0.5 | 4 | 3 | 6 | 110 |
| 6 | MP0036 | 0.5 | 4 | 4 | 2.5 | 17.9 |
| 7 | MP0036 | 0.5 | 4 | 4 | 2.5 | 43.94 |
| 8 | MP0036 | 0.5 | 5 | 4 | 2.5 | 58.35 |
| 9 | MP0036 | 0.5 | 5 | 4 | 2.5 | 67.17 |
| 10 | MP0035 | 0.1 | 4 | 12 | 2.5 | 110.8 |
| 11 | MP0038 | 0.5 | 4 | 3 | 6 | 91.28 |
| 12 | Only tendon - no device | | | | | 87.37 |
| 13 | MP0036 | 0.5 | 2 | 4 | 2.5 | 13.98 |
| 14 | MP0033 | 0.3 | 4 | 5 | 6 | 137.14 |
| 15 | MP0033 | 0.3 | 4 | 5 | 6 | 252.59 |
| 16 | One simple suture - no device | | | | | 22.59 |

Highest Load To Failure (LTF), trial 1: 110 N
Highest LTF, Trial 2: 252 N

What is claimed is:

1. A repair device for a torn tissue, comprising:
a) a tissue attachment unit comprising a tissue attachment element comprising an attachment head configured for securing said repair device to said torn tissue;
b) a clamp holding said tissue attachment unit, comprising the following separate elements: (i) a base configured to act as a positioning platform; (ii) side walls configured to secure the torn tissue in place and determine the attachment area; and (iii) a setter configured to hold the tissue attachment element; and
(c) a binder and/or an anchor, wherein:
said tissue attachment unit is configured to remain on the torn tissue while said clamp is configured to be removed after attachment of the tissue attachment unit to the torn tissue; and
said tissue attachment element is configured to be secured to only one side of the torn tissue.

2. The repair device of claim 1, wherein said attachment head is further configured for: (i) realigning and fixing torn edges or tips of said torn tissue back together; or (ii) connecting a torn edge or tip of said torn tissue to a bone.

3. The repair device of claim 1, wherein said device or at least said tissue attachment unit is made of a biocompatible material(s); and/or of a biodegradable material(s).

4. The repair device of claim 1, wherein said device or at least a part thereof comprises one or more drug releasing materials.

5. The repair device of claim 1, wherein said tissue is a torn tendon.

6. The repair device of claim 1, wherein said attachment head comprises spikes, hooks or rough surface(s), or a combination thereof.

7. The repair device of claim 1, wherein said attachment head is coated with drug releasing capabilities, healing/regeneration-mediated substances, immunodepression material(s), growth factors, stem cells, and/or anti-inflammatory substance(s).

8. The repair device of claim 7, wherein said attachment head comprises spikes and/or hooks, said spikes and/or hooks are configured to: (i) distribute the pulling force applied onto the attached tissue between all of said spikes and/or hooks; and/or (ii) be inserted into said torn tissue at a predefined angle, removed-therefrom if needed, and subsequently reinserted into said torn tissue.

9. The repair device of claim 8, wherein said spikes and/or hooks are differential in length, dispersion across the attachment head or in diameter.

10. The repair device of claim 8, wherein said spikes and/or hooks are personalized, perforated, foldable and/or extractable.

11. The repair device of claim 1, wherein said binder and/or anchor is: (i) present, and configured to secure said attachment element to a bone or to any other tissue, or to another repair device.

12. The repair device of claim 1, wherein said clamp is configured to define a tissue-attachment area at said torn tissue to which said attachment head binds/attaches.

13. The repair device of claim 1, wherein said side walls further comprise a mechanical tool that assists in spreading, stretching and/or straightening the tissue for attaching said tissue attachment unit thereto.

14. The repair device of claim 1, further comprising at least one of: an optic fiber, a light source, forceps or other grasping means, electromagnet, pressure sensors, tension sensors, and tendon conveyor belt.

15. The repair device of claim 1, further comprising at least one or more attachment heads.

16. The repair device of claim 1, wherein the tissue attachment unit further comprises an elongation tail.

17. The repair device of claim 16, wherein said binder and/or anchor is associated with said elongation tail.

18. The repair device of claim 1, wherein the tissue attachment unit sets the angle of the attachment head insertion into said tissue.

19. The repair device of claim 1, wherein said attachment head has a perforated structure for allowing tissue to grow therewithin.

20. The repair device of claim 1, wherein said attachment head is made of bio-degradable and/or biocompatible material.

21. The repair device of claim 1, wherein said attachment head is custom made according to patient's/tissue's anatomy and/or the tissue being repaired.

22. The repair device of claim 1, wherein said attachment head is perforated or net-like structured.

23. The repair device of claim 1, wherein the attachment head comprises a folding-, opening- and/or extractable-attachment head.

24. The repair device of claim 1, wherein the setter sets an angle of insertion of the tissue attachment element into said tissue.

25. A method for repairing a torn tissue, said method comprising:
   a) isolating said torn tissue;
   b) selecting an attachment area on said isolated tissue and securing the isolated tissue to the attachment area with the clamp of a repair device according to claim 1, wherein: the side walls secure the torn tissue and outline the selected attachment area, while the base serves as a tray on which said tissue lays;
   c) reviewing the selected attachment area, and making adjustments in the attachment area if needed;
   d) pressing the setter of said clamp holding an attachment head to thereby secure said attachment head to said torn tissue at said attachment area, wherein said pressing is carried out in a fixed movement, and wherein the base of said clamp provides a counter support when said setter is pushed against the torn tissue;
   e) fastening the attachment to its target area; and
   f) removing the clamp, leaving only the attachment element secured to said tissue.

26. The method of claim 25, wherein said tissue is a tendon.

27. The method of claim 25, wherein said attachment head comprises spikes and/or hooks and wherein in said (d) said setter participates in the actual pushing of the spikes and/or hooks of the attachment head into the tissue.

28. The method of claim 25, further comprising attaching another attachment head to said attachment area or another attachment area.

29. The method of claim 25, further comprising lifting the setter to extract said attachment head from said tissue, adjusting the attachment area, and repressing the setter after said fastening step or after said removing step by re-connecting the clamp to said attachment.

* * * * *